US00PP37104P2

(12) United States Plant Patent
Byrne et al.

(10) Patent No.: US PP37,104 P2
(45) Date of Patent: Nov. 25, 2025

(54) PEACH TREE NAMED 'TRH1A95'

(50) Latin Name: *Prunus persica*
Varietal Denomination: TRH1A95

(71) Applicant: The Texas A&M University System, College Station, TX (US)

(72) Inventors: David Hawkins Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/062,411

(22) Filed: Feb. 25, 2025

(51) Int. Cl.
*A01H 5/08* (2018.01)
*A01H 6/74* (2018.01)

(52) U.S. Cl.
USPC ..... Plt./190
CPC ..... *A01H 6/7463* (2018.05); *A01H 5/08* (2013.01)

(58) Field of Classification Search
USPC ..... Plt./190
See application file for complete search history.

(56) References Cited

U.S. PATENT DOCUMENTS

| | | | |
|---|---|---|---|
| PP12,965 | P2 | 9/2002 | Byrne |
| PP14,627 | P3 | 3/2004 | Byrne et al. |
| PP14,629 | P3 | 3/2004 | Byrne et al. |
| PP26,119 | P3 | 11/2015 | Byrne et al. |

OTHER PUBLICATIONS

Byrne, D. H. and U. Boonprakob. 2008. Thai Tiger low chill peach series. HortScience 43:2226-2227.
Rouse, R.E. and W.B. Sherman. 1989. TropicBeauty: A low-chilling peach for subtropical climates. HortSci. 24(1): 165-166.

*Primary Examiner* — Shubo Zhou
*Assistant Examiner* — Zachariah Allan Kay
(74) *Attorney, Agent, or Firm* — Dentons US LLP

(57) ABSTRACT

Disclosed is a new variety of *Prunus persica* named 'TRH1A95'. This new variety, which requires approximately 250 chilling units of dormancy, is considered to be a peach tree of very early season maturity, which produces orangish-yellow fleshed, sweet-acid fruit that are firm, with a 60-90% red to maroon blush over a yellow ground color, and suitable for fresh market use.

5 Drawing Sheets

Latin name of the genus and species of the plant claimed: *Prunus persica.*

Variety denomination: 'TRH1A95'.

BACKGROUND OF THE INVENTION

The present invention relates to a new and distinct asexually reproduced variety of peach tree (*Prunus persica*) designated 'TRH1A95'. 'TRH1A95' requires approximately 250 chilling units of dormancy, produces a firm, clingstone, orangish-yellow fleshed, sweet-acid peach with a 60-90% red to maroon blush over a yellow ground color that matures very early in the season. 'TRH1A95' was derived from a population created by crossing the low chill, yellow-fleshed, sweet-acid melting-fleshed peach 'Thai Tiger TXW1193-1' (Byrne, D. H. and U. Boonprakob. 2008. Thai Tiger low chill peach series. HortScience 43:2226-2227; not patented) with pollen of the medium-chill, medium acid, yellow-fleshed, non-melting flesh peach 'GulfKing' (Krewer, G., T. Beckman, J. Chaparro, and W. B. Sherman, 2005. 'Gulfking' and 'Gulfcrest', new peaches for the lower coastal plain. HortSci. 40(3):882; U.S. Plant Pat. No. 14,483). Resulting seed from the 'Thai Tiger TXW1193-1' x 'GulfKing' hybrid family were planted in 2011 in an experimental plot in Floresville, TX. 'TRH1A95' was marked for subsequent observation in 2013 and noted as having exceptional characteristics.

'TRH1A95' was asexually reproduced by bud grafting onto virus-free Nemaguard ("The Brooks and Olmo Register of Fruit and Nut Varieties," 3rd Ed., American Society of Horticultural Science Press, Alexandria, VA, 1997) peach at the nursery site in Oakdale, CA. The variety was subsequently planted and evaluated as two-year and older trees in Somerville (2017-2023), Texas and Caborca (2016-2018), Sonora, Mexico. This evaluation clearly demonstrated that the re-propagated trees were true to the characteristics of the original seedling in all observable aspects.

SUMMARY OF THE INVENTION

'TRH1A95' peach is characterized by producing clingstone, organish-yellow-fleshed, sweet-acid fruit that ripens very early in the season and produces a, firm fruit with a 60-90% red to maroon blush over a yellow ground color. In this regard, the present variety of peach tree bears fruit that are ripe for commercial harvesting and shipment in late April to early May, when the fruit is grown in the medium chill zone of Texas. 'TRH1A95' blooms 4-5 days after its female parent 'Thai Tiger TXW1193-1', and ~3 days before its pollen parent 'GulfKing'. It ripens ~2 weeks before its female parent and ~4 days before its pollen parent. 'TRH1A95' differs from its yellow-fleshed, sweet-acid, peach female parent as it ripens 2 weeks before it. It differs from its medium acid, yellow-fleshed, non-melting pollen parent as it is a peach which requires less chilling and has melting flesh. This new low-chill, orangish-yellow fleshed, clingstone, early-ripening, sweet-acid peach exhibits potential to be commercialized in mild winter regions that accumulate little chilling.

BRIEF DESCRIPTION OF THE DRAWINGS

This new variety of peach tree is illustrated by the accompanying photographs of plants grown in Somerville, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
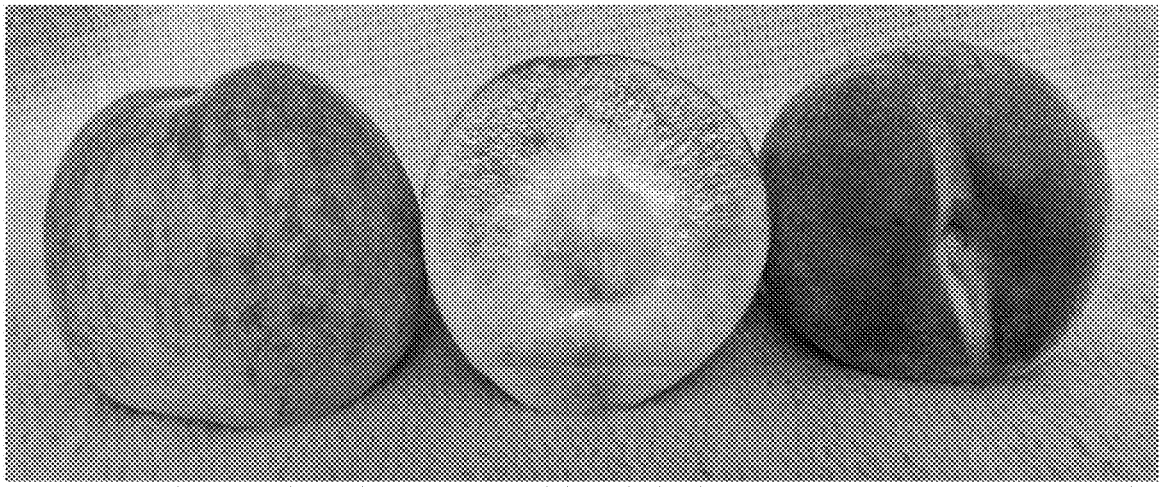
FIG. 1—Fruit of 'TRH1A95' produced in Somerville, Texas showing external and internal coloration.
Figure 2:
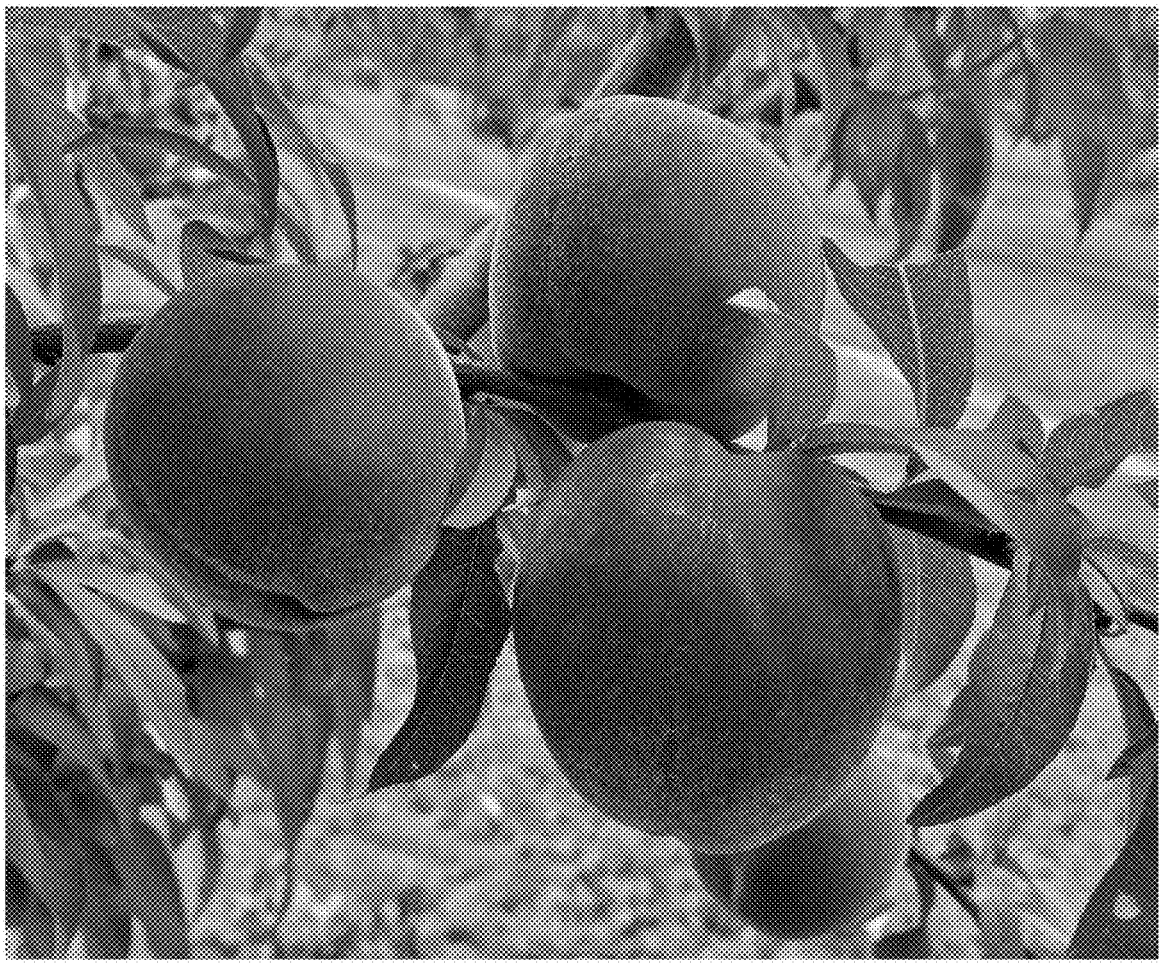
FIG. 2—'TRH1A95' fruit produced in Somerville, Texas showing shape and external coloration.
Figure 3:
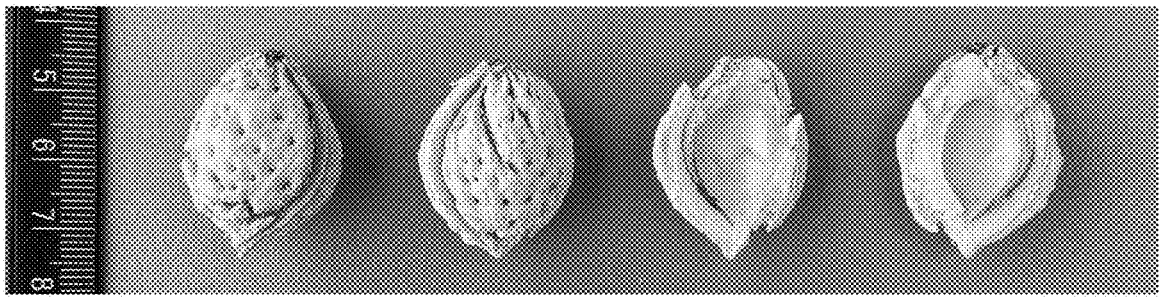
FIG. 3—Photograph of the endocarps of 'TRH1A95' peach. The ruler is in centimeters.
Figure 4:
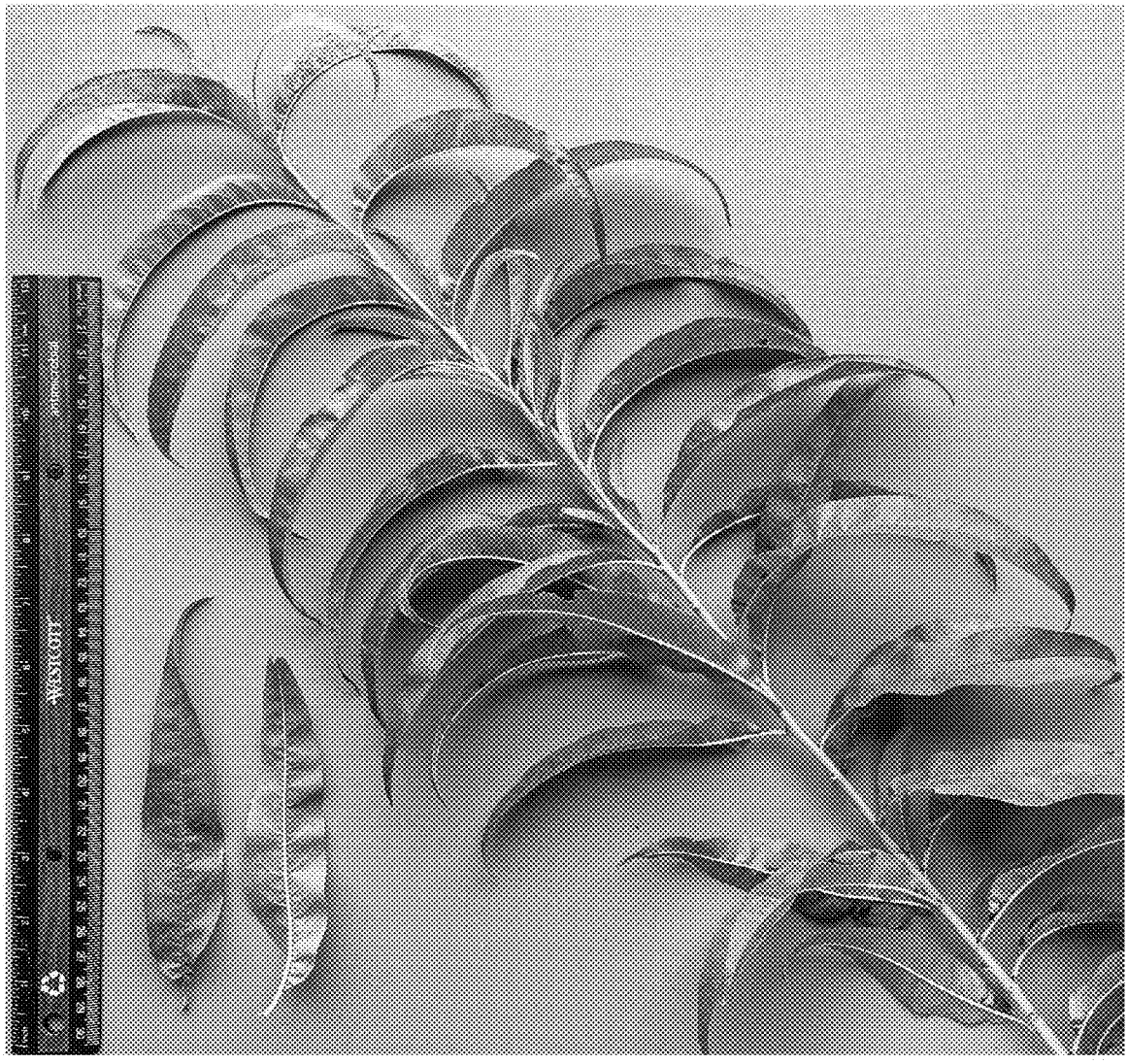
FIG. 4—A stem showing the leaves of 'TRH1A95' peach. The ruler is in centimeters.
Figure 5:
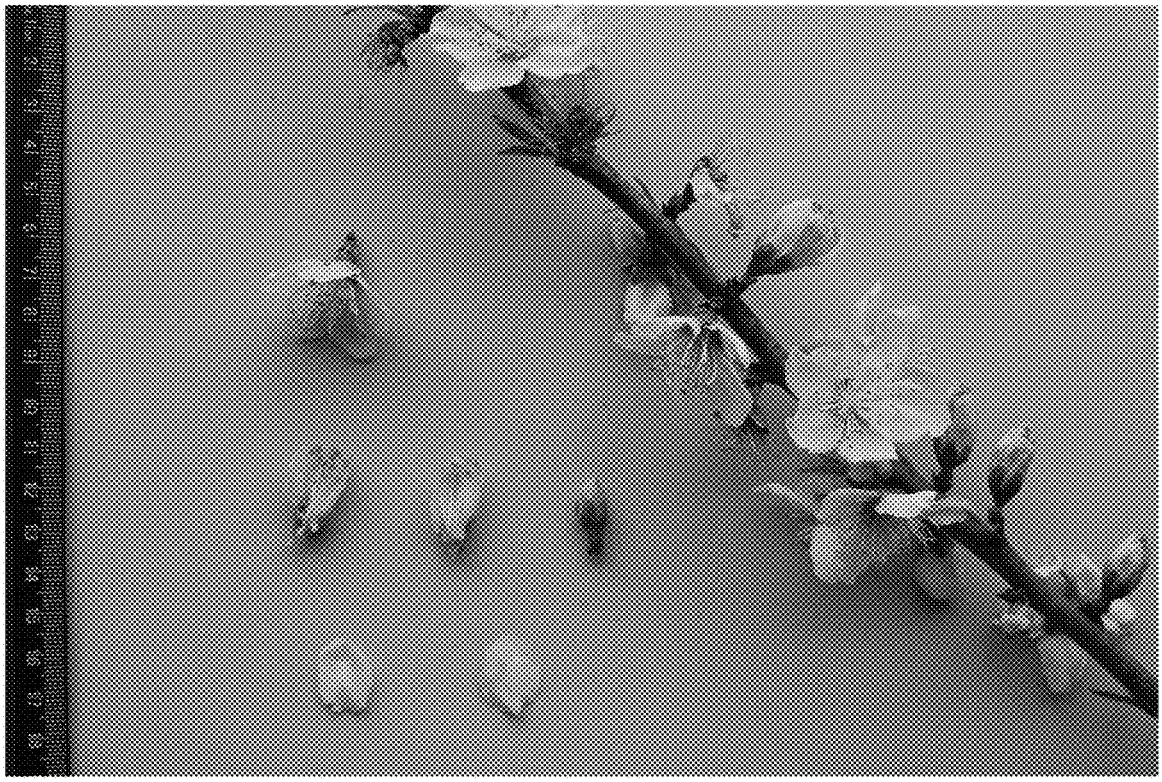
FIG. 5—A stem showing the flowers of 'TRH1A95' peach, wherein the upper sepals have some pubescence and the lower calyx cup does not. The ruler is in centimeters.

The following detailed description sets forth distinctive characteristics of 'TRH1A95', as observed under the ecological conditions prevailing at the experimental orchards in the medium chill zone of Texas (Pleasanton, and Somerville). 'TRH1A95' has not been observed under all possible environmental conditions, and the measurements given may vary when grown in different environments. Certain characteristics may also vary with plant age. All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars growing in the medium chill zone of Texas.

*Height*.—8 feet (2.4 m) on a 3-year old tree at the end of the 2024 growing season.

*Width*.—6 feet width (1.8 m) on a 3-year old tree at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. Trees often set more fruit than needed for a full crop.

*Shape*.—The 'TRH1A95' peach has been trained in an open center configuration and exhibits a semi spreading growth type as seen in peach varieties 'Texprince' (U.S. Plant Pat. No. 14,629) and 'Texking' (U.S. Plant Pat. No. 14,627).

*Current season growth*.—The current season growth for the new variety was approximately 1 to 3.5 feet (0.3-1.1 m). Vigor is medium compared to other common peach varieties grown in the medium chill zone of Texas.

*Regularity of bearing*.—Regular in the absence of temperatures of 28° F. or below during bloom and considered hardy in the medium chill zone of Texas.

Trunk:

*Size*.—Approximately 3.25 inches (8.3 cm) in diameter and 11 inches (27.9 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156B of the Greyed-White Group, 165A, 166A, 175A, 175B, 176A and 176B of the Greyed-Orange Group, 198D of the Greyed-Green Group, N200D of the Brown Group and 201D of the Grey Group.

Branches:

*Thickness*.—Average (about 4.5 to 5 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 7 to 14 mm in width and were approximately 1 to 2 mm in height.

*Current season shoots*.—Surface texture — Substantially glabrous.

*Internode length*.—Approximately 1.5 to 2.1 cm as measured in the middle of a current season stem.

*Color of mature branches*.—The predominant colors (RHS2001) are 156B of the Greyed-White Group, 156B, 172A, 172B, 173A, 175B, 175C, 176A, 176B and 177A of the Greyed-Orange Group, N200D of the Brown Group and 201D of the Grey Group.

Leaves:

*Size*.—Considered moderately large for the species. Leaf measurements have been taken from vigorous upright current season growth approximately at mid-shoot.

*Leaf length*.—Approximately 165 to 186 mm.

*Leaf width*.—Approximately 35 to 36 mm.

*Leaf thickness*.—Less than 1 mm.

*Leaf form*.—Lanceolate.

*Leaf tip form*.—Acuminate.

*Leaf upper surface color* (*RHS* 2001).—Green, 146A and 146B of the Yellow-Green Group.

*Leaf lower surface color* (*RHS*2001).—Green, 146A and 146B of the Yellow-Green Group.

*Leaf mid-vein color* (*RHS*2001).—Light yellow green, 145C, 150D and 154D of the Yellow-Green Group.

*Leaf margins*.—

*Form*.—Considered crenate.

*Uniformity*.—Considered generally uniform.

*Leaf petioles*.—

*Length*.—Approximately 9 to 10 mm.

*Thickness*.—Approximately 1.5 to 2 mm.

*Color* (*RHS*2001).—Pale green, 144A, 144B, N144D, 145A and 145B of the Yellow-Green Group.

*Leaf glands*.—

*Size*.—Approximately 2 to 2.5 mm in height and 1 mm in width.

*Number*.—Generally 2 per leaf.

*Type*.—Reniform.

*Color* (*RHS*2001).—Brown, 165B of the Greyed-Orange Group and N199C, and N199D of the Grey-Brown Group.

*Leaf stipules.*—

*Length*.—Approximately 8 to 10 mm.

*Form*.—Lanceolate.

*Color* (*RHS*2001).—Green, 144A, 144B, N144C, 146C and 146D of the Yellow-Green Group with reddish brown tips, 176A of the Greyed-Orange Group and 178A and 178B of the Greyed-Red Group when young. The stipules are early deciduous.

*Ratio of wood* (*leaf*) *buds to flowering buds*.—Generally 2 flower buds per vegetative bud.

Flowers:

*Floral buds*.—General — The floral buds are conic in form, and slightly appressed relative to the bearing shoot. Color (RHS2001) — The dormant floral buds are gray-brown, (approximately 156A and 156B of the Greyed-White Group, 165A and 166A of the Greyed-Orange Group, N199A of the Grey-Brown Group and 200A, 200B and 200C of the Brown Group). Bud Length — Approximately 4 to 6 mm. Bud Width — Approximately 2 to 2.5 mm.

*Blooming type*.—Considered early in relation to other peach cultivars commonly growing in the medium-chill zone of Texas. It blooms 3 to 5 days after 'TROPICPEACHONE' (U.S. Plant Pat. No. 12,965), 'TropicBeauty' (Rouse, R. E. and W. B. Sherman. 1989. 'TropicBeauty': A low-chilling peach for subtropical climates. HortSci. 24(1): 165-166) and 'Tex-First' (U.S. Plant Pat. No. 26,119). The estimated chilling requirement is about 250 chill hours.

*Flower type*.—Showy.

*Flower size*.—Flower diameter at full bloom is approximately 33 to 37 mm.

*Bloom quantity*.—Considered abundant.

*Flower bud frequency*.—Normally 1 to 2 per node.

*Petal size*.—Width — Approximately 13 to 14 mm. Length — Approximately 18 to 20 mm.

*Petal form*.—Broadly ovate.

*Petal count*.—Nearly always 5.

*Petal color* (*RHS*2001).—Medium pink when young (62C, 65B, 65C, 65D, 69B and 69C of the Red-Purple Group).

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear rounded.

*Flower pedicel*.—Length — Approximately 2 to 3 mm. Thickness — Approximately 1 mm. Color (RHS2001) — A light green (N144A, N144B, 145A and 145B of the Yellow.—Green Group).

*Floral nectaries*.—Color (RHS2001) — Medium orange (24A, 25A, 25B, 25C, N25A, N25B, 28A and 28B of the Orange Group).

*Sepals*.—

*Surface texture*.—The surface has a short, fine, wooly pubescence on the upper sepals. Size — Average and ovate in form. Color (RHS2001) — Maroon and green with white hairs (approximately 58A, 59C, 60A and 60B of the Red-Purple Group; 144B, N144D, 145A and 145B of the Yellow Green Group; 182A, 184A, 184B, 185A and 185B of the Greyed-Red and 155A, 155B, 155C and 155D of the White Group).

*Calyx cup* (*hypanthium*).—Surface Texture — Generally glabrous, wherein the lower calyx cup lacks pubescence. Color (RHS2001) — Maroon with green (approximately 58A, 59C, 60A and 60B of the Red-Purple Group; 144B, N144D, 145A and 145B of the Yellow Green Group and 182A, 184A, 184B, 185A and 185B of the Greyed-Red).

*Anthers*.—Color (RHS2001) — Light to medium yellow with orange (approximately 4A, 5A, 13A and 13B of the Yellow Group; 14A, 14B, 14C and 18A of the Yellow-Orange Group and 24A, 25A, 25B and N25B of the Orange Group).

*Pollen production*.—Pollen is abundant and yellow.

*Filaments*.—Size — Variable in length, approximately 12 to 15 mm, with the filaments equal to the pistil. Color — White (approximately 155A, 155B, 155C and 155D of the White Group).

*Pistil*.—General — Generally taller than the general anther height. Length — Approximately 18 to 19 mm, including the ovary. Color (RHS2001) — Considered a very light green with yellow when young (approximately 1C and 1D of the Green-Yellow Group; 2C, 3C, 3D, 5B, 5C and 5D of the Yellow Group and 154C and 154D of the Yellow-Green Group) and becoming darker with advancing senescence. Surface Texture — The variety has a long, silver white pubescent pistil (approximately RHS2001 155A. 155B, 155C and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in late April to early May. The average ripe date at Somerville was May 1$^{st}$.

*Size*.—General — Medium large to large for the season and considered uniform. Average Cheek Diameter — Approximately 55 to 62 mm. Average Suture Diameter — Approximately 52 to 60 mm. Average Axial Diameter — Approximately 49 to 58 mm.

*Fruit form*.—Generally considered truncate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Maroon. Generally, 53A of the Red Group, 59A of the Red-Purple Group and 183A, 183B, 185A and 187B of the Greyed-Purple Group.

*Ventral surface*.—Form — Considered uniform.

*Stem cavity*.—Width — Approximately 10 to 13 mm. Length — Approximately 17 to 19 mm. Depth — Approximately 7 to 10 mm.

*Fruit base*.—Flat.

*Fruit apex*.—Flat.

*Fruit stem*.—Length — 9 to 11 mm. Thickness — Approximately 3 to 4 mm. Color — Light green. N144D, 145A and 145B of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — No skin cracking observed. Skin Color — Generally — Variable, with approximately 60-90% of the fruit surface covered with medium red to maroon blush. Blush Color (RHS2001) — Medium red to maroon. Varying between N34A of the Orange-Red Group, 46A, 46B and 53A of the Red Group, 59A, 59B and 60A of the Red-Purple Group and 183A, 183B, 183C, N186C and 187B of the Greyed-Purple Group. Skin Ground Color (RHS2001) — Light to medium greenish yellow. 1C of the Green-Yellow Group and 3C, 4B and 5C of the Yellow Group.

*Flesh color* (*RHS*2001).—Orangish yellow. 12C, 13C and 13D of the Yellow Group and 14C, 14D, 15D, 16C and 18A of the Yellow-Orange Group.

*Flesh fibers*.—Present, numerous and lightly colored. These fibers are present throughout the flesh.

*Stone cavity color* (*RHS*2001).—Orangish yellow green. 1A of the Green-Yellow Group, 12C, 13C and 13D of the Yellow Group and 14C, 14D, 15D, 16C and 18A of the Yellow-Orange Group.

*Flesh texture*.—Generally, the flesh is considered firm and fine at commercial maturity.

*Ripening*.—Generally the fruit of the present variety ripens evenly.

*Flavor*.—Considered very sweet and rich, with slightly acidic flavor.

*Aroma*.—Pleasant and reasonably abundant.

*Eating*.—Generally considered very good, particularly for an early ripening variety.

Stone:

*Attachment*.—Clingstone at commercial maturity.

*Stone size*.—Length — Approximately 27 to 30 mm. Width — Approximately 19 to 22 mm. Thickness — Approximately 16 to 17 mm.

*Fibers*.—Generally a few medium length fibers are attached along the entire surface of the stone.

*Stone form*.—Varies from elliptical to ovate.

*Stone base angle*.—Considered narrow to medium.

*Stone shape*.—Considered ovoid.

*Stone surface*.—Surface Texture — Covered with single pits, rosettes of pits and chains of pits. Ridges — Numerous fine ridges are present basally and converge towards the base of the stone.

*Ventral edge*.—Present and small to medium in size.

*Dorsal edge*.—Shape — Grooved and having moderately rough edges.

*Stone color*.—The color of the dry stone is tan, 158A of the Yellow-White Group, 159A of the Orange-White Group and 164D and 165D of the Greyed-Orange Group. The color of the inside surface of the endocarp is primarily tan, 158A of the Yellow-White Group, 159A and 159B of the Orange-White Group and 164D and 165D of the Greyed-Orange Group.

*Tendency to split*.—No splitting of the pit observed.

*Kernel*.—The kernel fills the endocarp at harvest and measures approximately 3-5 mm in thickness, 9-10 mm in width, and 13-15 mm in length. The colors (RHS2001) of the fresh kernels are very light tan with brown veins 4D, 8D and 11D of the Yellow Group, 155B and D of the White Group, 158B, 158C, and 158D of the Yellow-White Group and 164A and 165B of the Greyed-Orange Group. When dried the shriveled kernels measure approximately 1 mm in thickness, 7-8 mm in width, and 13-14 mm in length. The colors of the shriveled kernels are light brown, primarily 164A, 165B, 165C, 167A, 167B and N167A of the Greyed-Orange Group.

*Use*.—The subject variety, 'TRH1A95', is considered to be a peach tree of early-season maturity, which produces acid-sweet, orangish-yellow fleshed fruit which are firm, and have a 60-90% red to maroon blush over a yellow ground color, and which are useful for fresh fruit market.

*Keeping quality*.—Average. Retains firmness and flavor after 14 days of refrigeration at 4-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 4-5° C.

Although the new variety of peach tree possesses the described characteristics when grown under the ecological conditions prevailing in the medium chill zone of Texas in Somerville, it will be understood that variations of the usual magnitude and characteristics incident to the changes in growing conditions, fertilization, pruning, and pest control are to be expected.

What is claimed is:

1. A new and distinct variety of peach tree named 'TRH1A95', as illustrated and described herein.

* * * * *